(12) United States Patent
Kozloski et al.

(10) Patent No.: US 10,734,119 B2
(45) Date of Patent: Aug. 4, 2020

(54) BODY CENTRIC COMMUNICATION AND AUTHENTICATION WITH AN ACTIVE IMPLANTED MEDICAL DEVICE

(71) Applicant: International Business Machines Corporation, Armonk, NY (US)

(72) Inventors: James R. Kozloski, New Fairfield, CT (US); Michael S. Gordon, Yorktown Heights, NY (US); Clifford A. Pickover, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 210 days.

(21) Appl. No.: 15/867,886

(22) Filed: Jan. 11, 2018

(65) Prior Publication Data

US 2019/0214150 A1   Jul. 11, 2019

(51) Int. Cl.
| | |
|---|---|
| *H04L 29/06* | (2006.01) |
| *H04W 12/06* | (2009.01) |
| *G16H 80/00* | (2018.01) |
| *G16H 40/67* | (2018.01) |
| *G16H 10/60* | (2018.01) |

(52) U.S. Cl.
CPC ............ *G16H 80/00* (2018.01); *G16H 10/60* (2018.01); *G16H 40/67* (2018.01); *H04L 63/083* (2013.01); *H04L 63/0853* (2013.01); *H04W 12/06* (2013.01); *H04L 2463/082* (2013.01)

(58) Field of Classification Search
CPC ........ G16H 80/00; G16H 40/67; G16H 10/60; H04W 12/06; H04L 63/083; H04L 63/0853; H04L 2463/082
See application file for complete search history.

(56) References Cited

U.S. PATENT DOCUMENTS

| | | |
|---|---|---|
| 6,961,448 B2 | 11/2005 | Nichols et al. |
| 7,319,962 B2 | 1/2008 | Goedeke et al. |
| 8,886,316 B1 | 11/2014 | Juels |
| 9,344,889 B2 | 5/2016 | Mancini et al. |
| 2005/0054926 A1 | 3/2005 | Lincoln |
| 2012/0010680 A1* | 1/2012 | Wei ................... A61N 1/36007 607/40 |
| 2014/0074493 A1 | 3/2014 | Schneider et al. |
| 2015/0035643 A1 | 2/2015 | Kursun |

(Continued)

OTHER PUBLICATIONS

BSI, "Active Implantable Medical Devices", https://www.bsigroup.com/en-US/medical-devices/Technologies/Active-Implantable-Medical-Devices/, The British Standards Institution 2018, Accessed on Jan. 10, 2018, 8 pages.

(Continued)

*Primary Examiner* — Michael R Vaughan
(74) *Attorney, Agent, or Firm* — Scully, Scott, Murphy & Presser, P.C.; JoAnn Kealy Crockatt

(57) ABSTRACT

An implantable device coupled with an integrated circuitry, is operable to receive signals representing a human body action. The implantable device may be further operable to authenticate the signals. Responsive to authenticating the signals, the implantable device may be further operable to perform a device action associated with the implantable device. The implantable device may include a medical device that detects physical conditions of a body.

18 Claims, 4 Drawing Sheets

(56) References Cited

U.S. PATENT DOCUMENTS

| | | | |
|---|---|---|---|
| 2016/0250490 A1* | 9/2016 | Hoffman | A61N 1/37252 607/60 |
| 2018/0153477 A1* | 6/2018 | Nagale | G16H 30/40 |
| 2018/0247024 A1* | 8/2018 | Divine | G06T 11/60 |
| 2019/0015669 A1* | 1/2019 | Muessig | A61B 5/0028 |
| 2019/0188368 A1* | 6/2019 | Hastings | H04L 63/0272 |

OTHER PUBLICATIONS

McIntyre, D.A., "The Eleven Most Implanted Medical Devices in America", http://247wallst.com/healthcare-economy/2011/07/18/the-eleven-most-implanted-medical-devices-in-america/print/, 24/7 Wall St., Jul. 18, 2011, Accessed on Jan. 10, 2018, 6 pages.

Clery, D., "Could a wireless pacemaker let hackers take control of your heart?", http://www.sciencemag.org/news/2015/02/could-wireless-pacemaker-let-hackers-take-control-your-heart, Science, Feb. 9, 2015, Accessed on Jan. 11, 2018, 2 pages.

Wadhwa, T., "Yes, You Can Hack a Pacemaker (and Other Medical Devices Too)", https://www.forbes.com/sites/singularity/2012/12/06/yes-you-can-hack-a-pacemaker-and-other-medical-devices-too/#1eee92656853, Forbes, Dec. 6, 2012, Accessed on Jan. 10, 2018, 3 pages.

Kim, S.-E., et al., "Sound transmission through the human body with digital weaver modulation (DWM) method", Systems Conference (SysCon), 2014 8th Annual IEEE, Mar. 31-Apr. 3, 2014, 4 pages.

Patently Mobile, "Samsung Invents Implantable Medical Device for the Brain", http://www.patentlymobile.com/2012/04/samsung-invents-implantable-medical-device-for-the-brain.html, Patently Mobile, Apr. 24, 2012, Accessed on Jan. 10, 2018, 4 pages.

Dubey, K., "Medical implants vulnerable to attack, MIT and UMass have a solution", http://www.techshout.com/science/2011/15/medical-implants-vulnerable-to-attack-mit-and-umass-have-a-solution/, TechShout.com, Accessed on Jan. 10, 2018, 4 pages.

Goodin, D., "Brave New World—medical devices use biometrics to prevent hack attacks: Wearable devices can use heart rate to prevent tampering by malicious hackers", https://arstechnica.com/security/2012/08/medical-device-hack-attacks/, Ars Technica, Aug. 7, 2012, Accessed on Jan. 10, 2018, 3 pages.

Hei, X., et al., "Security for Wireless Implantable Medical Devices", Springer Briefs in Computer Science, 2013, https://books.google.com/books?id=QeZHAAAAQBAJ&pg=PA7&lpg=PA7&dq=biometric+password+medical+devices&source=bl&ots=teDBMVppsT&sig=ajFJU-#v=onepage&q=biometric%20password%20medical%20devi%20ces&f=false, Accessed on Jan. 11, 2018, 10 pages.

Camara, C., et al., "Security and privacy issues in implantable medical devices: A comprehensive survey", Journal of Biomedical Informatics, Received Aug. 21, 2014, Available online Apr. 24, 2015, pp. 272-289, vol. 55.

* cited by examiner

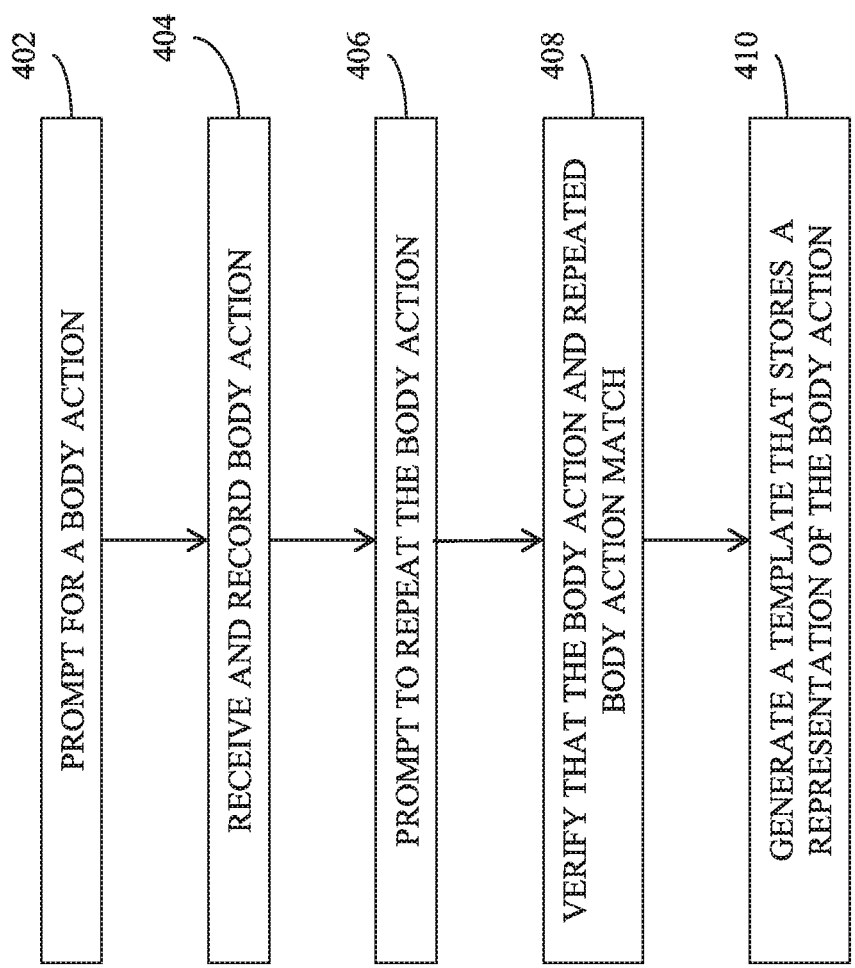

BODY CENTRIC COMMUNICATION AND AUTHENTICATION WITH AN ACTIVE IMPLANTED MEDICAL DEVICE

FIELD

The present application relates generally to implantable medical devices and communicating with the implantable devices.

BACKGROUND

The Active Implantable Medical Device (AIMD) Directive 90/385/EEC defines an active implantable medical device as "any active medical device which is intended to be totally or partially introduced, surgically or medically, into the human body or by medical intervention into a natural orifice, and which is intended to remain after the procedure." As one of the highest risk categories of device, active implantable medical devices (AIMDs) are subject to rigorous regulatory controls during both pre-market and post-market periods. The regulatory controls set out in the AIMD Directive also apply to all accessories that are used to enable the device to operate as intended, for example, leads, programmers, controllers, battery packs, software applications, implant kits and refill kits.

Examples of AIMDs may include implantable cardiac pacemakers, implantable defibrillators, left ventricular assist device, leads, electrodes, adaptors for implantable cardiac pacemakers and defibrillators, brachytherapy, haemodynamic support, cochlear implants, implantable infusion pumps and accessories, implantable glucose monitors, micro electro-mechanical systems (MEMS), implantable gastric stimulator, neuroprosthetics, transcutaneous vagus nerve stimulation, insulin pumps, neurostimulators, various drug delivery systems, and others. The devices may be used to treat chronic ailments such as cardiac arrhythmia, diabetes, and Parkinson's disease. Many AIMDs are enabled with wireless communication capabilities and can communicate with an external device. With the rise in use of AIMDs, however, security becomes a critical issue, as attacks on AIMDs may harm the patient wearing the device.

BRIEF SUMMARY

Body centric communication and authentication method and apparatus may be provided. The apparatus, in one aspect, may include an implantable device coupled with an integrated circuitry. The implantable device may be built to perform a device action associated with the implantable device. The implantable device may be operable to receive signals representing a human body action, and to authenticate the signals. Responsive to authenticating the signals, the implantable device may be further operable to perform the device action.

The body centric communication and authentication method, in one aspect, may include receiving by an implantable device coupled with an integrated circuitry, signals representing a human body action. The method may also include authenticating by the implantable device the signals. The method may further include, responsive to authenticating the signals, performing a device action by the implantable device.

The signals, in one aspect, comprise a second set of signals of a two-factor authentication comprising a first set of signals and the second set of signals, the second set of signals sent within a human body and wherein the implantable device is triggered to receive the second set of signals by the first set of signals of the two-factor authentication sent from a device external to the apparatus.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

BRIEF DESCRIPTION OF THE DRAWINGS

FIG. 4 is a flow diagram illustrating a method of generating a template that stores a representation of the body action for authentication in one embodiment, for instance, for teaching or programming the active implanted medical device to recognize the body action.

DETAILED DESCRIPTION

Figure 1:
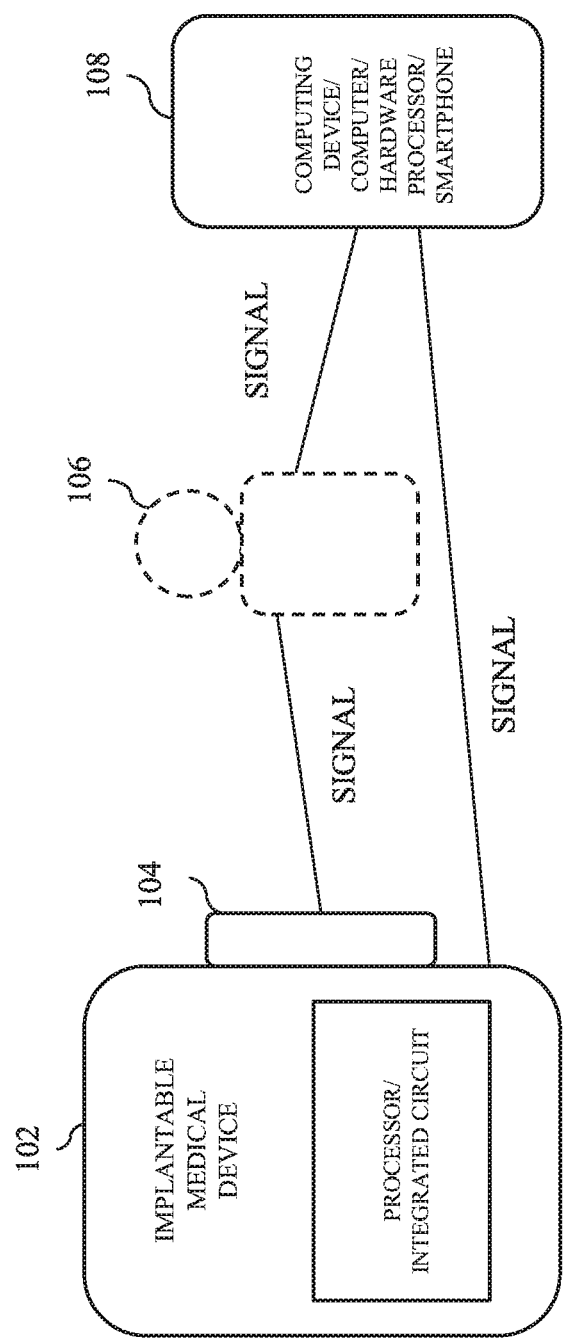
FIG. 1 is a diagram illustrating system components in one embodiment of the present disclosure.

System, method and techniques are disclosed that provide secure communication and/or authentication to a device (e.g., medical device) integrated with a human body. An electronic active medical device, e.g., which is implantable within a human body, is enabled to communicate with and/or authenticate a command based on a "body method" of a patient. For instance, a "body method" of a patient is used to communicate with and/or authenticate a command to the device. Based on the authentication, the device proceeds to take an action associated with the command or communication. A "body method" includes one or more body actions performed in a series or as a pattern of actions.

The device that can be integrated with a human body, in one embodiment, may include any AIMDs, for example, described above, implantable defibrillators; leads, electrodes, adaptors for implantable cardiac pacemakers and defibrillators; implantable neuro stimulator systems; brachytherapy; haemodynamic support; cochlear implants; implantable infusion pumps and accessories; implantable glucose monitors; micro electro-mechanical systems (MEMS); implantable gastric stimulator; neuroprosthetics; transcutaneous vagus nerve stimulation; smart pill, and/or others.

In one embodiment, the "body method" of patient authentication may include any of: tapping on a part of a body, changing characteristics of breathing (e.g., holding breath for a time duration (e.g., 3 seconds) and then releasing the breath), flexing of muscles (e.g., tightening of abdomen muscles for a time duration (e.g., 3 seconds)), a pattern of coughing, saying sounds or phonemes, blinking of eyes in a predetermined pattern, wriggling of toes in a particular defined order, wriggling of fingers in a particular defined order, bowing, jumping, rotating or shaking or waving or raising or lowering limbs, squatting, pirouetting, a movement of a body core, a movement of a body limb, another voluntary action or movement, and/or others. Such body method may be subtle and not easily captured by an outsider person, or may be obvious but intended for use only in the privacy of a doctor's examining room. For example, a user may wish to keep the user's authentication key difficult for others to see (e.g., unlike waving of hands in the air, which can be obvious to those nearby). For instance, flexing of a stomach muscle or holding one's breath for 3 seconds may be difficult to detect to anyone observing the patient. On the other hand, a doctor may be present in closed examining room and instruct the user to execute the pattern, and the pattern may then comprise obvious "body methods."

In one embodiment, the "body method" may include a sequence of body actions, each of which may likely occur throughout the normal course of the day, but when composed into the specified sequence, are unlikely to occur in that sequence.

In one embodiment, the "body method" includes the following properties: the body method is under voluntary control of the patient; the body method is detectable by the device and discriminable from other voluntary or involuntary body actions; the body method is difficult to spoof by anyone other than the owner of the body; body method is unusual and not likely to occur throughout the day for other reasons than to control the device.

In one embodiment, a prompt to the patient to provide the body method of patient authentication may be provided by a smartphone or the like, or another computer device, and the body method may be performed with or without the supervision or collaboration with a healthcare professional.

In one embodiment, a prompt to the device may be provided by a healthcare professional, for example, using methods such as an electronic signal itself comprising a code for secure prompting, which puts the device in a mode in which the patient authentication may be received by the device. In this way the authentication becomes a two-factor authentication requiring both the standard unlocking of the device for modification by the healthcare provider, and an acknowledgment or confirmation that this is desired by the patient using the patient's body method authentication. This two-factor authentication method then has added security to prevent malicious hacking of the medical device using electronic methods only, intended to spoof or exploit the standard authentication by the healthcare provider.

In one embodiment, the device may also incorporate a "fall detector" (e.g., an accelerometer) to estimate that a patient has fallen. An accelerometer coupled with the device may also be used to detect the body action, e.g., detect tightening of muscles, reflexes from coughing, and/or other body actions. A device like a pacemaker or pump may also serve a dual purpose to help detect falls, for example, experienced by patients, for instance, an elderly or one with irregularities in the heart, insulin level, and/or brain function or a person experiencing low blood pressure, and/or others. In another embodiment, the fall can be reported to people on a predetermined list (e.g., family members, the patient's doctor) or emergency medical personnel.

Device action, or the action the device performs responsive to the proper authentication and/or communication, may include (but are not limited to), providing an electrical signal, providing a chemical signal, changing a setting or device parameters, turning the device on or off, and/or others.

The device detection and/or recognition of speech may be enhanced with consideration of acoustical properties inside the human body. The implantable device may learn about the tone, vibrations and sound generated when a particular patient speaks. In that way, the patient authentication for an external command to the implantable device may include a predetermined spoken word, phrase, sequence of sounds, and/or others. The implantable device learns the acoustical properties of the patient speaking those words, phrase, and/or sequence of sounds, e.g., a predefined key word or sound so that it responds to the patient and not to anyone else speaking the same words In one embodiment, the authentication may serve as a user authentication or also as a specific command to the device, like changing the parameters on a pacemaker. For setting changes, additional input other than the single "body method" authentication or communication may be provided, the body method being a part of an overall authorization protocol, e.g., submitted with other inputs, e.g., including computer-based inputs which may depend on the severity of the change.

The device itself may optionally provide tactile or other feedback to request a user authentication or to confirm the receipt of a user authentication or transmission. For example, a part of a device may safely vibrate for a time period (e.g., half-second), which the user may feel or detect to represent the confirmation or act as a request that the user performs to authenticate the command.

The device may communicate to the user to confirm receipt of a body message (or to make a request of the user) using a sound transmission system that transmits sound wirelessly to the ears without making any other noise outside of the body. The system in one embodiment may utilize the human body as a sound transmission medium. For example, considering the human body as a nonlinear medium with nonlinear characteristics, two ultrasonic waves with different frequencies are transmitted into the body. The difference frequency signal between the two original ultrasonic waves is generated during the propagation process and audible to a user. For example, a single sideband modulation (SSB AM) method may be used as a modulation scheme. SSB AM method can minimize the noise which occurs in the process of generating audible sound. To make a SSB AM modulator with a higher degree of accuracy, a digital weaver modulation (DWM) method may be adopted. DWM method enables a sharp cutoff filter to be implemented without increasing computational complexity in the digital signal processor (DSP). An equalizer filter which compensates the distortions in the ultrasonic transducer may be also designed. Such methodology allows for sound transmission to a human without cable line required in conventional earphones.

In one embodiment, the body method of patient authentication may adopt a device such as a transmitter to block a possibly unauthorized signal (e.g., for a short amount of time in a public place). Generally, the body method of patient authentication in one embodiment may also serve as a temporary medical protection safety lockout system.

FIG. 1 is a diagram illustrating system components in one embodiment of the present disclosure. A device such as a medical device 102 may include an interface 104 that can receive or detect a body action or a series of body actions, for authenticating the requests to change a setting on the medical device 102 and to perform a device action responsive to authenticating the body action or the series of body actions. The interface 104 may receive signals generated by the body actions and authenticate those signals by matching the signals with a predefined set of signals. Responsive to authenticating the body action, the medical device 102 is activated or triggered to perform its device actions. In one embodiment the interface is trained to recognize the body actions. For example the interface asks the user or patient to perform the body actions and to indicate when the body actions are concluded. Then the interface asks the patient to repeat the body actions to determine whether they were input correctly, for example, in a similar fashion as password input for computer systems or smart phone applications. The determination of a match to a previously learned body action may be by means of signal processing of time series recordings from any of accelerometers, microphones, piezo-electric sensors, stress meters and/or others, and can include analysis techniques such as cross-correlation, spectral analysis, and wavelet decomposition to determine if the recorded body action falls within a threshold of tolerance for the match.

As described above, the medical device 102 is implantable in a human body 106 and can detect body actions based on signals generated, for example, within the human body 106. In this way, a patient may communicate with the medical device 102, for example, when implanted within the human body 106. In one aspect, a smartphone 108, the implanted device 102, or another computer device may notify a user to begin performing a body action.

The implantable medical device with an interface 104 may include a processor or integrated circuits to perform the functions described above. In some embodiments, the processor may include electronic circuitry including, for example, programmable logic circuitry, field-programmable gate arrays (FPGA), or programmable logic arrays (PLA) that perform aspects of the present invention in one embodiment. The functions described above may be programmed into the integrated circuits of a processor of the implantable medical device 102, or loaded from memory, storage device, or network or combinations thereof.

The device at 108, which may send a notification signal to the user 106 to perform a body action for authenticating with the implantable medical device 102, may include a smartphone comprising at least a processing unit or circuitry, and for example, running an app or application. In another aspect, the device at 108 may include any of personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. In another aspect, the device at 108, may send a notification signal to the user 106 to perform a body action, by sending a signal to the implantable device 102, which may then send a second signal to the user, e.g., within the user's body. Transmission of signals may be performed wirelessly, in one embodiment. Other communication techniques may be employed.

The device 108 may be part of the implantable device 102 in the case that it might be a miniaturized signal processing ASIC or another device specifically engineered to authenticate the body action.

Figure 2:
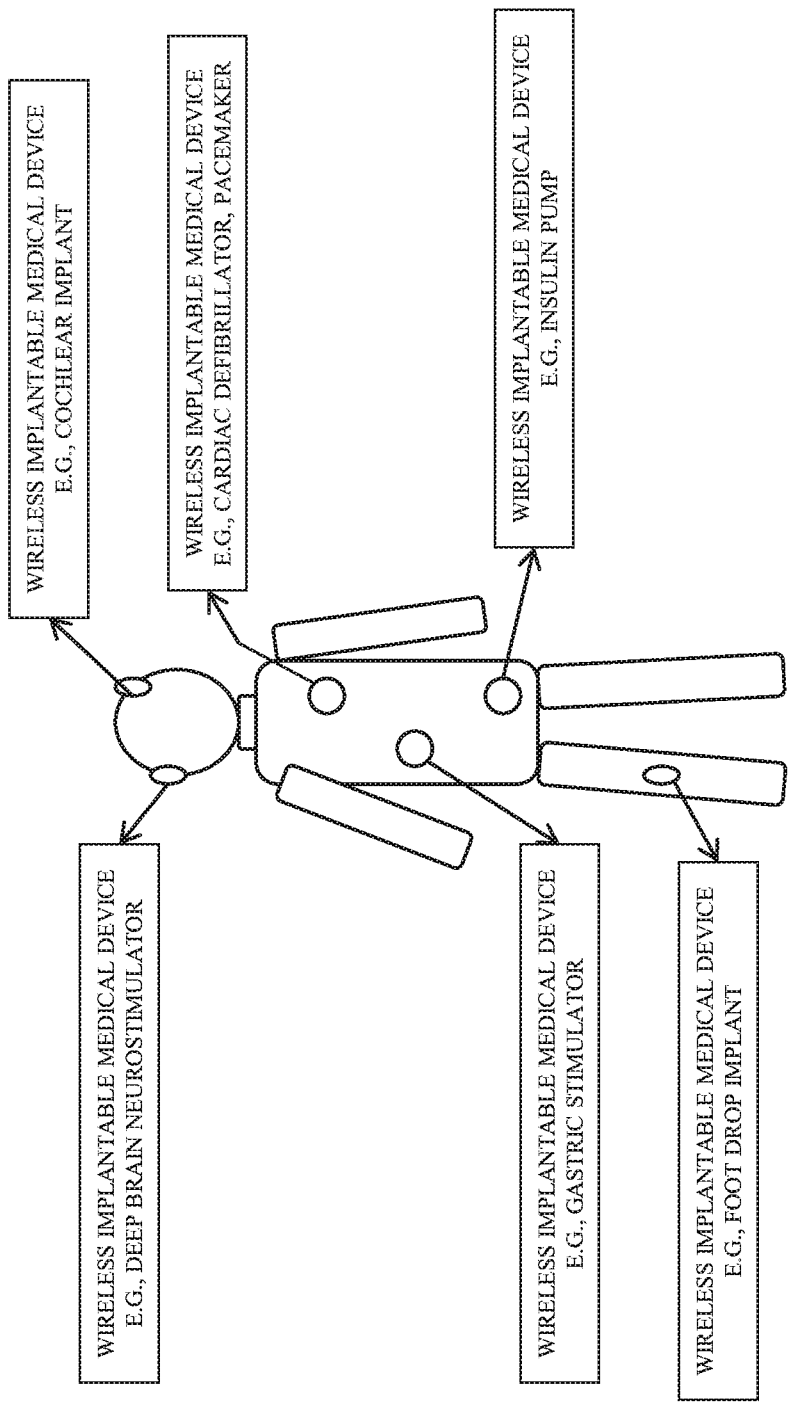
FIG. 2 is a diagram illustrating examples of implantable medical devices in one embodiment.

FIG. 2 is a diagram illustrating examples of implantable medical devices in one embodiment. Such devices may include, but are not limited to, a deep brain neurostimulator, gastric stimulator, foot drop implant, cochlear implant, cardiac defibrillator, pacemaker, and insulin pump. Such a device when implanted in a human body is able to detect movement or other actions of the human body (also referred to as a body action). Based on the detected body action authenticating successfully, the device activates itself to perform its device action. In some embodiments, if the authentication is not performed successfully, within a specified period of time, the device does not perform the action.

Figure 3:
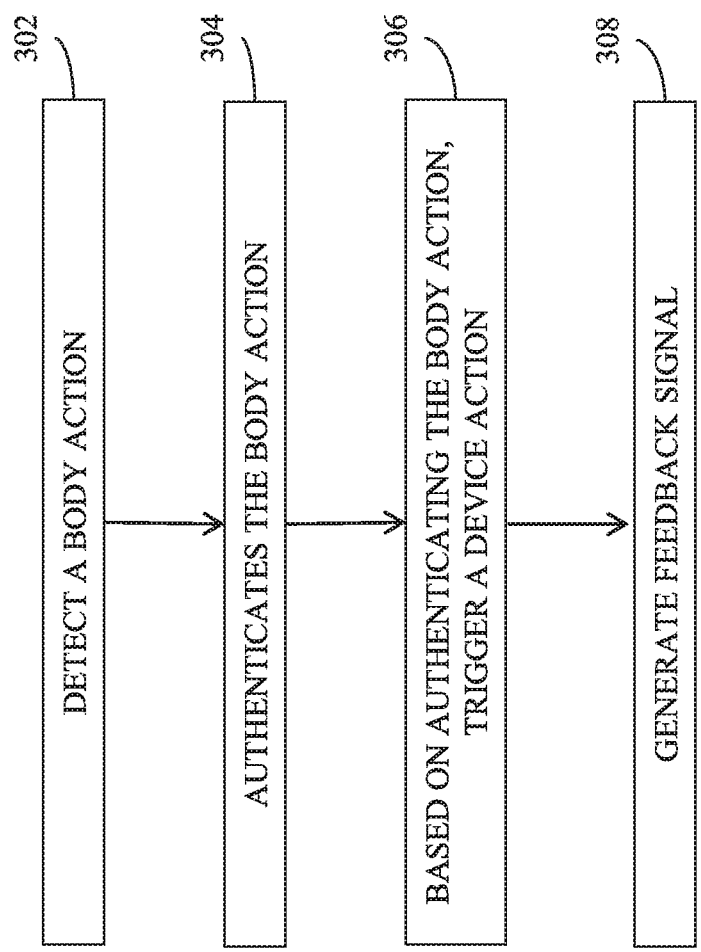
FIG. 3 is a flow diagram illustrating a communication method of an active implanted medical device in one embodiment of the present disclosure.

FIG. 3 is a flow diagram illustrating a communication method of an active implanted medical device in one embodiment of the present disclosure. At 302, an active implanted medical device detects a body action performed by a human body, for example, by detecting signals representing the body action. The signals may be a second set of signals of a two-factor authentication which includes authentication of a first set of signals and the second set of signals. The second set of signals may be sent within a human body and the implantable device is triggered to receive the second set of signals by the first set of signals of the two-factor authentication sent from a device external to the apparatus. Detection of the body action for example, may include the implanted medical device detecting a pattern of movement or sound signals made by the human body. The implanted device may be placed into a mode in which it is receiving the body action, for example, by an electronic unlocking of this function by a healthcare professional, and may then begin recording the body action using one of several positional, acceleration, rotational, deformational, and/or stress measures, and/or others. These recordings may then be processed using signal processing techniques such as correlational analysis to determine if the body action matches a template.

The template may be provided by a previous training of the system by the user, or by a programming of the device using a standard template. For example, the template may be generated based on training of the system, which may include the following procedure: The user may be asked to generate a body action for a specific implanted device; the body action generated by the user may be recorded using a microphone, accelerometer, camera, or another component that can record a body action; the user is requested to repeat the body action so that it can be confirmed that the user issues the same body action. This training of the system may be performed by a computing device such as a smartphone, a personal computer, a laptop, or another computing device, for example, in cooperation with the implanted medical device. In another embodiment, the training may be performed by the device itself.

In some embodiments, the template may be updated by each subsequent body action, and in this way the template may be updated to reflect changing kinematics of the user due to normal changes in the user's body actions due to aging, degeneration, or disability.

Examples of the active implanted medical device may include, but is not limited to, any of implantable cardiac pacemakers, implantable defibrillators, left ventricular assist device, leads, electrodes, adaptors for implantable cardiac pacemakers and defibrillators, brachytherapy, haemodynamic support, cochlear implants, implantable infusion pumps and accessories, implantable glucose monitors, micro electro-mechanical systems (MEMS), implantable gastric stimulator, neuroprosthetics, transcutaneous vagus nerve stimulation, insulin pumps, neurostimulators, various drug delivery systems, and others. Examples of the body action may include, but is not limited to, tapping on a part of a body, changing characteristics of breathing (e.g., holding breath for a time duration (e.g., 3 seconds) and then releasing the breath), flexing of muscles (e.g., tightening of abdomen muscles for a time duration (e.g., 3 seconds)), a pattern of coughing, making a series of sounds such as saying sounds or phonemes, blinking of eyes in a predetermined pattern, wriggling of toes in a particular defined order, wriggling of fingers in a particular defined order, bowing, jumping, rotating or shaking or waving or raising or lowering limbs, squatting, pirouetting, a movement of a body core, a movement of a body limb, another voluntary action or movement, and/or others.

At 304, the active implanted medical device authenticates the body action. If the body action is the same action specified by the template or within a defined analyzed level of tolerance when compared to the template using standard signal processing techniques, the authentication is completed.

At 306, responsive to authenticating the body action, the active implanted medical device triggers itself to perform a device action. Examples of the device action may include, but is not limited to, providing an electrical signal (e.g., indicating a body condition), providing a chemical signal (e.g., that represents a body condition), changing a setting or device parameter, turning on or off the device, and/or others.

At 308, the device itself may optionally provide tactile or other feedback signal, for example, responsive to authentication. In another embodiment, the device may send such tactile of other feedback signal to request a user authentication or to confirm the receipt of a user authentication or transmission. For example, a part of a device may safely vibrate for a time period (e.g., half-second), which the user may feel or detect to represent the confirmation, denial, or other feedback.

FIG. 4 is a flow diagram illustrating a method of generating a template that stores a representation of a body action or actions for authentication in one embodiment, for instance, for teaching or programming the active implanted medical device to recognize the body action. At 402, the user may be prompted by an implanted device or another computing device, to perform a body action or actions, and for example, to indicate that the body action is concluded. At 404, the body action or actions (for example, signals representing the body action or actions) are received and recorded. At 406, the user is prompted to repeat the body action. The signals representing that repeated body action is also received and may be recorded. At 408, the body action and the repeated body action are compared to verify that they match. At 410, responsive to determining that the two body actions (first performed and the repeated body actions) match, the signals representing the body action are saved as a template. For instance, a template may be created to store the signals. As another example, an existing template may be used to store the signals. As also described above, whether two body actions match or not match may be determined based on performing signal processing of time series recordings from any of accelerometers, microphones, piezo-electric sensors, stress meters, and/or others, and may include analysis techniques such as cross-correlation, spectral analysis, and wavelet decomposition to determine whether the recorded body action falls within a threshold of tolerance for the match. The template may be stored on a memory coupled with the implantable medical device. In one aspect, the implantable medical device may perform the method shown in FIG. 4. In another aspect, another computing device may perform the method.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. An apparatus, comprising:
an implantable device coupled with an integrated circuitry,
the implantable device built to perform a device action associated with the implantable device,
the implantable device operable to receive signals representing a human body action,
the implantable device further operable to authenticate the signals,
responsive to authenticating the signals, the implantable device further operable to perform the device action,
wherein the signals comprise a second set of signals of a two-factor authentication comprising a first set of signals and the second set of signals, the second set of signals sent within a body and the implantable device is triggered by receipt of the first set of signals of the two-factor authentication sent from a device external to the apparatus, to receive the second set of signals,
wherein the implantable device is further operable to provide a feedback to the human body, the feedback confirming the receipt of the second set of signals,
the implantable device further operable to block a signal at least temporarily in a public place.

2. The apparatus of claim 1, wherein the signals are sent within a human body and the implantable device is operable to receive the signals within the human body.

3. The apparatus of claim 1, wherein the implantable device is a medical device that detects physical conditions of a human body.

4. The apparatus of claim 1, wherein the implantable device comprises any one or more of implantable cardiac pacemaker, an implantable defibrillator, an implantable neuro stimulator, a implantable defibrillators, leads, electrodes, adaptors for implantable cardiac pacemakers and defibrillators, brachytherapy, haemodynamic support, cochlear implants, implantable infusion pumps and accessories, implantable glucose monitors, micro electro-mechanical systems (MEMS), implantable gastric stimulator, neuroprosthetics, transcutaneous vagus nerve stimulation, and smart pill.

5. The apparatus of claim 1, wherein the human body action comprises any one or more of a voluntary action, a tapping on the human body, a changing of characteristics of breathing, a flexing of muscles, a coughing, a saying sounds or phonemes, a blinking of eyes in a predetermined pattern, a wriggling of toes in a defined order, a wriggling of fingers in a defined order, a movement of a body core, a movement of a body limb.

6. The apparatus of claim 1, further comprising an accelerometer coupled with the implantable device, the accelerometer allowing the implantable device to detect a falling motion of a human body.

7. The apparatus of claim 1, further comprising an accelerometer coupled with the implantable device, the accelerometer allowing the implantable device to detect a body action.

8. The apparatus of claim 1, wherein the device action comprises any one or more of transmitting an electrical signal representing a physical condition of a human body, transmitting a chemical signal representing a physical condition of a human body, and setting a parameter of the implantable device.

9. The apparatus of claim 1, wherein the implantable device generates and provides a feedback signal responsive to authenticating the human body action.

10. A method, comprising:
receiving by an implantable device coupled with an integrated circuitry, signals representing a human body action;
authenticating by the implantable device the signals; and
responsive to authenticating the signals, performing a device action by the implantable device,
wherein the signals comprise a second set of signals of a two-factor authentication comprising a first set of signals and the second set of signals, the second set of signals sent within a body and the implantable device is triggered by receipt of the first set of signals of the two-factor authentication sent from a device external to the apparatus, to receive the second set of signals,
wherein the implantable device is further operable to provide a feedback to the human body, the feedback confirming the receipt of the second set of signals,
the implantable device further operable to block a signal at least temporarily in a public place.

11. The method of claim 10, wherein the implantable device is implanted into a human body and the human body action is performed voluntarily within the human body.

12. The method of claim 10, further comprising detecting a falling motion by the implantable device.

13. The method of claim 10, wherein an instruction to perform the human body action is provided by a smartphone.

14. The method of claim 10, wherein the implantable device is a medical device that detects physical conditions of a human body.

15. The method of claim 10, wherein the implantable device comprises any one or more of implantable cardiac pacemaker, an implantable defibrillator, an implantable neuro stimulator, a implantable defibrillators, leads, electrodes, adaptors for implantable cardiac pacemakers and defibrillators, brachytherapy, haemodynamic support, cochlear implants, implantable infusion pumps and accessories, implantable glucose monitors, micro electro-mechanical systems (MEMS), implantable gastric stimulator, neuroprosthetics, transcutaneous vagus nerve stimulation, and smart pill.

16. The method of claim 10, wherein the human body action comprises any one or more of a voluntary action, a tapping on the human body, a changing of characteristics of breathing, a flexing of muscles, a coughing, a saying sounds or phonemes, a blinking of eyes in a predetermined pattern, a wriggling of toes in a defined order, a wriggling of fingers in a defined order, a movement of a body core, a movement of a body limb.

17. The method of claim 10, wherein the device action comprises any one or more of transmitting an electrical signal representing a physical condition of a human body, transmitting a chemical signal representing a physical condition of a human body, and setting a parameter of the implantable device.

18. The method of claim 10, further comprising generating and providing a feedback signal by the implantable device responsive to authenticating the human body action.

* * * * *